(12) United States Patent
Cattaneo et al.

(10) Patent No.: US 9,233,013 B2
(45) Date of Patent: Jan. 12, 2016

(54) STENT AND METHOD FOR THE PRODUCTION OF SUCH A STENT

(75) Inventors: Giorgio Cattaneo, Karlsruhe (DE); Kirsi Schüssler, Pfinztal (DE)

(73) Assignee: Acandis GmbH & Co. KG, Pfinztal (DE)

( * ) Notice: Subject to any disclaimer, the term of this patent is extended or adjusted under 35 U.S.C. 154(b) by 1161 days.

(21) Appl. No.: 12/918,668

(22) PCT Filed: Feb. 12, 2009

(86) PCT No.: PCT/EP2009/000996
§ 371 (c)(1),
(2), (4) Date: Nov. 2, 2010

(87) PCT Pub. No.: WO2009/103457
PCT Pub. Date: Aug. 27, 2009

(65) Prior Publication Data
US 2011/0046718 A1 Feb. 24, 2011

(30) Foreign Application Priority Data

Feb. 22, 2008 (DE) .......................... 10 2008 010 507

(51) Int. Cl.
*A61F 2/82* (2013.01)
*A61F 2/90* (2013.01)
(Continued)

(52) U.S. Cl.
CPC ... *A61F 2/90* (2013.01); *A61F 2/91* (2013.01); *A61F 2002/30014* (2013.01);
(Continued)

(58) Field of Classification Search
CPC ........................................................ A61F 2/82
USPC ........................................................ 623/1.16
See application file for complete search history.

(56) References Cited

U.S. PATENT DOCUMENTS

| 6,428,569 B1 | 8/2002 | Brown |
| 2002/0107562 A1 | 8/2002 | Hart et al. |

(Continued)

FOREIGN PATENT DOCUMENTS

| DE | 101 44 430 A1 | 3/2003 |
| DE | 10 2006 007 231 A1 | 8/2007 |

(Continued)

OTHER PUBLICATIONS

Int'l Search Report issued on May 27, 2009 in Int'l Application No. PCT/EP2009/000996.

(Continued)

*Primary Examiner* — Thomas J Sweet
*Assistant Examiner* — Matthew Schall
(74) *Attorney, Agent, or Firm* — Panitch Schwarze Belisario & Nadel LLP

(57) ABSTRACT

A stent having a tubular lattice structure includes lattice elements, webs (10), and cells (11) delimited by the lattice elements. The lattice structure is transferred into a compressed state having a relatively smaller cross-sectional diameter and into an expanded state having a relatively larger cross-sectional diameter. Flexible contact elements (12) are associated with the lattice elements. The contact elements are adapted for transferring radial forces onto a vessel wall (20) and extending on the outer circumference of the lattice structure substantially in the longitudinal direction of each associated lattice element. The contact elements (12) are wider in each case than the associated lattice elements, at least in sections.

25 Claims, 4 Drawing Sheets

(51) Int. Cl.
*A61F 2/91* (2013.01)
*A61F 2/30* (2006.01)

(52) U.S. Cl.
CPC ............... *A61F 2002/30016* (2013.01); *A61F 2002/30018* (2013.01); *A61F 2002/30148* (2013.01); *A61F 2002/30168* (2013.01); *A61F 2002/30172* (2013.01); *A61F 2002/30324* (2013.01); *A61F 2002/30558* (2013.01); *A61F 2230/0017* (2013.01); *A61F 2230/0043* (2013.01); *A61F 2230/0052* (2013.01); *A61F 2250/0018* (2013.01); *A61F 2250/0019* (2013.01); *A61F 2250/0036* (2013.01); *A61F 2250/0073* (2013.01)

(56) References Cited

U.S. PATENT DOCUMENTS

2007/0239261 A1  10/2007  Bose et al.
2010/0009142 A1  1/2010   Quandt et al.
2010/0049310 A1  2/2010   Quandt et al.
2010/0204779 A1  8/2010   Schuessler et al.

FOREIGN PATENT DOCUMENTS

DE  10 2006 029 831 A1  1/2008
DE  10 2007 019 772 A1  10/2008
WO  2006/125022 A2     11/2006

OTHER PUBLICATIONS

Written Opinion issued on May 27, 2009 in Int'l Application No. PCT/EP2009/000996.

Office Action Issued Dec. 3, 2008 in German Appln. Ser. No. 10 2008 010 507.4.

Int'l Preliminary Report on Patentability Issued Sep. 7, 2010 in Int'l Application No. PCT/EP2009/000996; Written Opinion.

State of the art

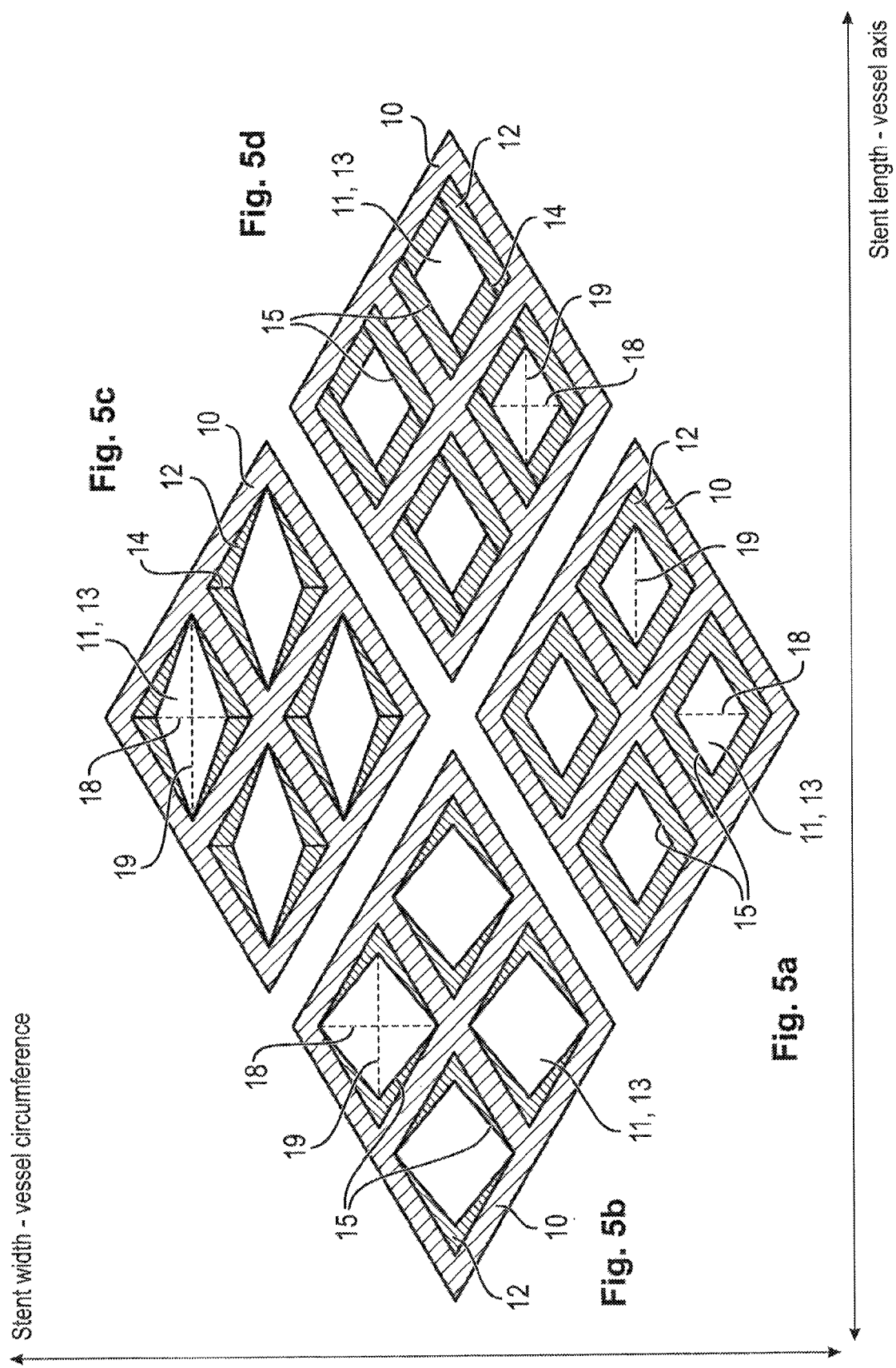

STENT AND METHOD FOR THE PRODUCTION OF SUCH A STENT

CROSS-REFERENCE TO RELATED APPLICATIONS

This application is a Section 371 of International Application No. PCT/EP2009/000996, filed Feb. 12, 2009, which was published in the German language on Aug. 27, 2009, under International Publication No. WO 2009/103457 A1 and the disclosure of which is incorporated herein by reference.

BACKGROUND OF THE INVENTION

The present invention relates to a stent according to the preamble of the independent claim(s) of the present application and a method for the production of such a stent. Such a stent is disclosed for example in U.S. Pat. No. 6,428,569 (Brown).

Stents that are formed from a tubular lattice structure are used for widening and supporting blood vessels. Stenoses or aneurysms in particular are treated in this manner. Stenoses, i.e., narrowing of blood vessels, lead downstream to a restricted supply of the tissue with nutrients. The constriction is opened-up and stabilized using a stent such that an adequate blood flow is guaranteed. Aneurysms represent bulges in blood vessels that lead to severe stress on the blood vessel walls. These bulges may grow with time and cause rupturing of the vessel wall. By placing an appropriate stent in a blood vessel in the region of an aneurysm, the flow of blood in the aneurysm is reduced or stopped such that coagulation of the blood takes place within the aneurysm which prevents it from growing further During and after implantation, a stent exerts a radial force on the adjacent blood vessel wall. This force is distributed over the number of webs around the stent's circumference. With a relatively small number of webs, each of these exerts a high force on the blood vessel wall, which is undesirable since this may give rise to irritation of or injury to the blood vessel. Due to the resulting inflammatory response, there is an increased risk of restenosis, i.e., renewed narrowing of the blood vessel, after it has been widened by means of a stent. Therefore, in post-published German patent application no. 10 2007 019 772 referring back to the applicant, it is proposed to increase the number of webs such that the forces acting on the vessel wall are better distributed and thus each individual web exerts a lesser force on the vessel wall.

U.S. Pat. No. 6,428,569 (Brown) referred to at the outset describes a stent with a fine-mesh lattice structure, the webs of which have a very small width. The small contact surface between the individual web and the vessel wall arising as a result of the small web width leads to the local pressure, which is exerted on the vessel wall at a specific radial force per web, being relatively high.

The width and number of the webs cannot, however, be increased at will without impairing the stent's implantability. In order to implant the stent, it is compressed and placed inside a catheter which is used to introduce the stent into the blood vessel. The maximum web width or the maximum number of webs is limited by the geometric constraints that are set by the size of the catheter or the size of the blood vessels to be treated.

Added to this is the fact that the force is not transmitted evenly over the entire outer surface of the webs because the webs cut into the vessel wall due to the high local pressure. As a result, the radial force transmitted to the vessel wall is greater in the region of the longitudinal edges of the webs than in the inner region of the webs. The stress concentration thus resulting in the region of the longitudinal edges increases the risk of restenosis.

This effect, which increases with greater web width, is illustrated, for example, in FIG. 1a of the present application, which shows a partial cross-section through a stent according to the prior art in the implanted state. Webs s are in contact with a vessel wall g and transmit a radial force F onto vessel wall g that is brought about due to the stent's expansion. In FIG. 1a, radial force F is indicated by arrows whereby the magnitude of the force is expressed in each case by the length of the arrow. Due to the high local pressure which webs s transmit onto vessel wall g, this wall is stretched and deformed whereby the maximum deformation occurs in the region of longitudinal edges a of webs s. This leads to the transmission of force occurring mainly in the marginal regions or on longitudinal edges a of webs s.

Overall there are, therefore, two structural measures which lead to the required result of reducing the loads on a blood vessel wall by means of a stent. On one hand, an increased number of webs over the cross-section of the stent improves the homogeneous distribution of forces over the vessel wall such that the local forces per web are reduced. On the other hand, a reduction of the local pressures that act on the vessel wall in the region of the individual webs is achieved by increasing the web width and thus the contact area. The combination of both measures, i.e. increasing the number of webs while simultaneously enlarging the web width, is limited by the geometric restrictions during implantation.

BRIEF SUMMARY OF THE INVENTION

Thus the object of the present invention is to provide a stent with a tubular lattice structure that reduces the load on the vessel walls and the risk of restenosis without significantly impairing the stent's implantability in the process. In addition, the object of the present invention is to provide a method for the production of such a stent.

The idea of the present invention is to provide a stent having a tubular lattice structure, comprising lattice elements, in particular webs, and cells delimited by the lattice elements, wherein the lattice structure may be transferred into a compressed state having a relatively smaller cross-sectional diameter and into an expanded state having a relatively larger cross-sectional diameter. In this case flexible contact elements are associated with the lattice elements, said contact elements being adapted for transferring radial forces onto a vessel wall and extending on the outer circumference of the lattice structure substantially in the longitudinal direction of each associated lattice element, wherein the contact elements are wider in each case than the associated lattice elements, at least in sections.

The stent according to the present invention, by comparison with the prior art, enables the arrangement, in the expanded state, of many webs with large contact areas between the webs and the vessel wall whereby the stent is additionally easily implantable.

To do this the present invention provides for contact elements disposed on the stent's outer circumference, said contact elements being associated with the lattice elements. The contact elements are wider than the lattice elements. As a result, a contact area enlarged by comparison with the simple lattice element is achieved between stent and vessel wall in the implanted or expanded state. The contact elements that are at least wider in sections signify that said elements, at least in the stent's expanded state, protrude over at least one edge of each associated lattice element and therefore enlarge the contact area, formed by the lattice element, between lattice element and vessel wall or overall between stent and vessel wall. The width of a contact element is considered first and foremost to be the extension of the contact element substantially perpendicular to its longitudinal extension. The present invention is not restricted to this, but generally includes contact elements that enable an enlargement of the contact area in the expanded state compared to the contact area in the compressed state.

Good implantability of the stent according to the present invention is retained despite the enlarged contact area since the contact elements are flexible and are able to deform on crimping or compression of the stent. Therefore, with the stent according to the present invention, it is possible to achieve diameters that are small enough for them to be implanted using conventional feeding systems or catheters. The flexible contact elements stretch during implantation due to the movement of the lattice elements and/or due to an inherent movement when using a shape memory material and take up their active positive. In the active position, the contact elements are stretched by the lattice elements and/or by corresponding conditioning and form the contact area via which the radial force is transmitted to the vessel wall.

It is possible due to the reversibly enlargeable contact area, which is achievable due to the flexible contact elements, to reduce the width of the lattice elements without any increase in the local pressure exerted by the individual lattice elements on the vessel wall.

In this way, the contact area between stent and vessel wall may be increased in conjunction with a high number of lattice elements since, with the stent according to the present invention, the width of the individual lattice elements may be reduced without any diminishing of the effective contact area in the implanted state.

Overall, due to the flexible contact elements, the stent according to the present invention enables a variable contact area for transmitting the radial force, said contact area approximating to the area of the lattice elements in the compressed state.

A further advantage of the stent according to the present invention is that the flexible contact elements adapt better than the rigid webs to the curved vessel wall such that the adverse stress peaks along the longitudinal edges occurring with the rigid webs are prevented.

The stent according to the present invention is particularly effective in the treatment of stenoses inside a blood vessel since the load on the blood vessel and the risk of injury is reduced due to the large contact area between the flexible contact elements and the vessel wall. In addition, using the stent according to the present invention, the treatment of aneurysms is also improved since the aneurysm is greatly hydraulically decoupled from the blood flow in the blood vessel due to the large proportion of the stent's closed circumferential surface. This encourages coagulation of the blood in the aneurysm and prevents a rupture of the aneurysm wall.

The stent according to the present invention is suitable for the treatment of vulnerable plaques or soft plaques. This is an accumulation of soft tissue inside a blood vessel wall. Unlike stenoses, in this case there is no narrowing of the vessel's diameter. Nevertheless, there is a danger of vascular occlusions as the soft tissue inside the vessel wall is only separated from the blood stream by a thin membrane. Injury of this thin membrane may lead to the plaque being released as a result of which smaller vessels may become blocked downstream. The thin membrane of a soft plaque on the vessel wall may be stabilized using the stent according to the present invention without the forces transmitted via the webs leading to injury of the membrane unlike with known stents. Stents according to the present invention may also be used to treat harder plaques, for example calcium deposits in blood vessels. By minimizing the local forces in the region of the lattice elements, it is possible with harder plaques to prevent deposits, for example calcium deposits, from being severed and transported particle by particle into smaller vessels with the blood stream.

Preferably, the lattice elements in each case together with an associated contact element form a substantially T-shaped or L-shaped cross-section, at least in sections. In the T-shaped cross-section, the contact elements protrude over both sides of the associated lattice elements, in particular symmetrically. In the L-shaped cross-section, the contact elements only protrude over one side of the associated lattice elements.

The contact elements may be wider in each case than each associated lattice element by at least 10%, in particular at least 15%, in particular at least 20%, in particular at least 30%, in particular at least 40%, in particular at least 50%, in particular at least 60%, in particular at least 70%, in particular at least 80%, in particular at least 90%, in particular at least 100%. The contact elements are preferably no more than 500%, in particular at most 400%, in particular at most 300%, in particular at most 200%, in particular at most 100% wider than each lattice element. In this manner, a sufficient increase in the contact area between the outer surface of the stent and the inner surface of the vessel wall is achieved such that the load on the vessel wall due to the radial pressures occurring locally, i.e., in the region of the lattice elements, is minimized.

In general, specification of the width of the contact elements relates to the region or section of the contact element that has the greatest width in relation to the lattice element or that projects furthest beyond the width of the lattice element. This applies to both contact elements that project on both sides (T-shape) and also that project on one side (L-shape) beyond each associated lattice element.

Where the projection is on both sides, the sides of the contact element protruding over the lattice element may project varyingly far beyond the lattice element. The distance of the one longitudinal edge of the contact element from the lattice element may be smaller or greater than the distance of the other longitudinal edge from the lattice element. The distance of both longitudinal edges from each other may be greater overall than the width of the associated lattice element in this region. The distance between one longitudinal edge of the contact element and the lattice element may vary along said lattice element.

In addition, the width of one contact element or a plurality of contact elements may be variable over the stent's circumference and/or length. This means that the width of a contact element changes in the stent's circumferential and/or longitudinal direction. The same applies to the width of a plurality of contact elements. As a result, it is possible to adjust regions with differing flexibility or differing strength. Moreover, the stent may be adapted locally to areas of the vessel wall to be treated. For example, the contact elements in regions of the stent which cover an aneurysm after implantation may be wider such that the relatively wider contact elements efficiently separate the aneurysm from the blood stream in the vessel and thus have a positive effect on the flow conditions within the aneurysm. The contact elements, for example, may be relatively narrower in regions of the stent that are disposed in the region of junctions between vessels after implantation such that an adequate blood flow is ensured in the vessel branching off.

In a preferred embodiment of the stent according to the present invention, the cells of the lattice structure each have an opening which is delimited by the contact elements of those lattice elements that form each cell. In this case, the openings are disposed on the outer circumference of the lattice structure and face towards the inner wall of the vessel in the implanted state. The openings may be adapted in each case to the contour of the cell. The openings are substantially diamond-shaped. The diamond shape enables the lattice structure to be transferred in a particularly advantageous manner into the compressed or expanded state. This is particularly the case when the cells delimited by the lattice elements also have a substantially diamond-shaped structure, whereby the invention is not restricted thereto but also includes stents with an open cell structure. The lattice structure with diamond-shaped openings may be transferred into the compressed state particularly easily as the diamond shape's diagonal aligned in the lattice structure's longitudinal direction is lengthened and the diamond shape's diagonal aligned in the circumferential direction is shortened. On the other hand, lengthening of the diamond shape's diagonal aligned in the circumferential direction with simultaneous shortening of the diamond shape's diagonal aligned in the lattice structure's longitudinal direction brings about an expansion of the stent.

In a further preferred embodiment of the present invention, the contact elements each have at least one longitudinal edge which extends parallel to a longitudinal axis of each associated lattice element. Moreover, the contact elements may each have at least one longitudinal edge which is disposed at an angle to the longitudinal axis of each associated lattice element. In general, the width of a contact element and/or the distance between one longitudinal edge of the contact element and the associated lattice element may vary along said lattice element. For example, the contact element may be narrower in one region of the lattice element than in another region of the lattice element or web. In particular, for example, a contact element associated with a lattice element may be exactly as wide on a first axial end of the lattice element and, for example, may be twice as wide or wider than the lattice element on a second axial end. At the same time, the contact element on the first end may terminate with the lattice element (gap=0) and on the second end may protrude beyond it by a certain amount, for example by the width of the lattice element.

In addition, the contact elements may each have two longitudinal edges which are disposed parallel to one another and/or are disposed at an angle to a longitudinal axis of each associated lattice element. The contact elements may form substantially rectangular strips which are substantially disposed diagonally to each associated lattice element. This ensures that stresses on or damage to the contact element due to transferring the lattice structure into a compressed or expanded state are reduced since appropriately selecting the angle between contact element and lattice element prevents stretching or extension of the contact element on compression or expansion of the lattice structure. The appropriate angle depends primarily on the stent geometry in each case and the desired ratio between the cross-sectional diameter in the expanded and compressed state and may be determined empirically, for example by means of experiments.

In a preferred embodiment of the present invention, the contact elements are joined so as to be overlapping and/or adjacent to each other in corner regions of the cells or are joined to each other. It is ensured by means of the overlapping or adjacent arrangement of the contact elements in the corner region of the cells that, on transferring the lattice structure into a compressed or expanded state, the contact elements are displaceable in relation to each other such that excessive stress, in particular extension, of the contact elements due to movement of the lattice structure is prevented. The combination of overlapping contact elements and adjacent contact elements may be particularly advantageous. With a diamond-shaped structure of the cells, for example, the opposing corners of the lattice structure in the circumferential direction may have adjacent contact elements and the opposing corners of the lattice structure in the longitudinal direction may have overlapping contact elements. On transferring the lattice structure into a compressed state, the distance between the opposing corners of the lattice structure in the longitudinal direction increases such that the contact elements in the region of the opposing corners in the circumferential direction are pulled apart. If the contact elements there are arranged adjacently, the contact elements may slide apart. This prevents extension of the contact elements. On the other hand, the contact elements disposed on the opposing corners in the longitudinal direction may overlap such that the contact elements do not fold during compression of the lattice structure but rather slide over one another.

Preferably, the contact elements have a height or wall thickness between 0.5 µm and 100 µm, in particular 1 µm and 50 µm, in particular 2 µm and 30 µm, in particular 3 µm and 20 µm, in particular 5 µm and 10 µm. The heights or wall thicknesses of the contact elements referred to ensure high stability and at the same time low weight such that the blood vessel is adequately supported on one hand, and on the other an additional load on the blood vessel brought about due to the stent's weight is reduced.

The height of the contact elements preferably corresponds to at least 0.5%, in particular at least 1%, in particular at least 2%, in particular at least 5%, in particular at least 10%, of the height of each associated lattice element. Especially preferably, the height of the contact elements corresponds to at most 50%, in particular at most 40%, in particular at most 30%, in particular at most 20%, in particular at most 15%, in particular at most 10%, of the height of the lattice elements. Accordingly, the ratio of the height of the contact elements (KE) to the height of each associated lattice element (GE), i.e., KE:GE, may, for example, be at least 1:20 and at most 1:10. The height of the lattice elements varies depending on application case of the stent to be used, in particular depending on the desired location of use.

The height of one or a plurality of contact elements may be variable both over the circumference and/or length of the stent and also over the width and or length of the contact element(s). The concept of a stent with contact elements of varying height or with contact elements having different wall thicknesses enables, for example, the stent to have different strength and flexibility properties in certain regions. For example, the stent may be provided with thinner contact elements in sections such that the stent adapts flexibly to a vessel curvature or vessel junction in the implanted state. The adjustment of different wall thicknesses can be carried out within a single contact element and/or for a plurality of contact elements.

In a preferred embodiment of the present invention, the contact elements have a greater height or wall thickness in the region of each associated lattice element than in an outer region, i.e., in a region distant from each associated lattice element or in the region of the contact elements which projects beyond each associated lattice element. In this way, the transmission of force to the vessel wall is improved, in particular is distributed more evenly, since the transition from one region, in which the force is transmitted to the vessel wall, to a region in which fewer or no forces are transmitted (outer region or opening delimited by contact elements) is continuous. Increased local pressures on the outer regions or longitudinal edges of the contact elements are thus efficiently prevented.

Furthermore, the contact elements may comprise a shape memory material, in particular a nickel-titanium alloy. The desired shape of the contact elements in the expanded or implanted state may be specified in this manner during production of the contact elements. Under the influence of certain ambient conditions, in particular the body temperature, the contact elements assume the shape imprinted on them during production which simplifies implantation of the stent. The use of shape memory materials for the contact elements is particularly advantageous if the lattice structure or lattice elements are also produced from a shape memory material. In this way it is possible to insert the stent according to the invention into a blood vessel in a compressed state where the stent expands automatically inside the blood vessel because of the body temperature and thus widens a stenosis, for example, without any additional mechanical exertion of force.

In general, by appropriately selecting the material, for example a nickel-titanium alloy or a polymer compound, and the wall thickness of the contact elements, it is possible to achieve an optimum compromise between the flexibility and strength of the contact elements such that, on one hand, the contact elements adapt well to the contour of the vascular wall in the implanted state and, on the other, the radial forces arising are transferred so as to be distributed substantially evenly over the entire outer surface. In this case, a person skilled in the art will select the material and the configuration of the dimensions of the contact elements based on each application or purpose of the stent. In general, selection is regardless of the stent's desired diameter in the expanded or implanted state and may be made empirically by the person skilled in the art based on experiments. At the same time, the use of biodegradable materials, such as magnesium or magnesium alloys, may also be considered.

Especially preferably, the contact elements have a structured surface, in particular pores or grooves. A structured surface promotes endothelialization, i.e., the growth of cells similar to the vessel on the structured surface, which lead in the treatment of aneurysms, for example, to a closure of the aneurysm inlet or aneurysm neck. In addition, the structured surface may be used as a depot for medically active substances, for example stem cells, genes as therapeutic agents, anti-coagulants or other substances. Compared to known stents, a larger dispensing area is provided in this case for such substances due to the wider contact elements.

In addition, the idea of the present invention is to provide a method for the production of a stent according to the invention, in which flexible contact elements are joined with lattice elements or are produced integrally with the lattice elements in such a manner that at least one contact element is associated in each case with a lattice element, the contact element protruding beyond the lattice element's cross-section. If the flexible contact elements are joined to the lattice elements, this is preferably carried out by means of laser beam micro welding or bonding. Preferably a sputtering process, in particular magnetron sputtering or ion beam sputtering, is used for production of the contact elements, whereby the contact elements may be sputtered either directly onto the lattice elements or may be sputtered integrally with the lattice elements. The method according to the present invention enables the implementation of a large contact area between stent and vessel wall in the implanted or expanded state, whereby a large number of webs is provided around the stent's circumference such that the radial forces acting on the vessel wall are evenly distributed around the circumference.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the following, the invention is explained in greater detail based on embodiments with reference to the associated schematic drawings. In the drawings:

FIGS. 5a-d is in each case a view from above of a plurality of adjacent cells according to different embodiments of the present invention in an expanded state.

DETAILED DESCRIPTION OF THE INVENTION

Certain terminology is used in the following description for convenience only and is not limiting. The word "inwardly" refers to a direction toward the geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Figure 1B:
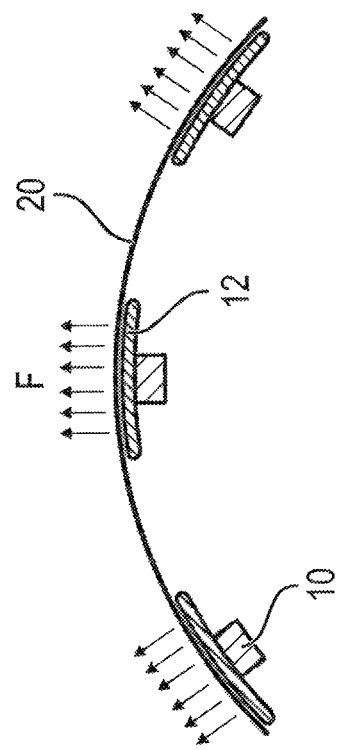
FIG. 1b is a partial cross-sectional view through a stent according to a preferred embodiment the present invention in the implanted state.
Figure 2B:
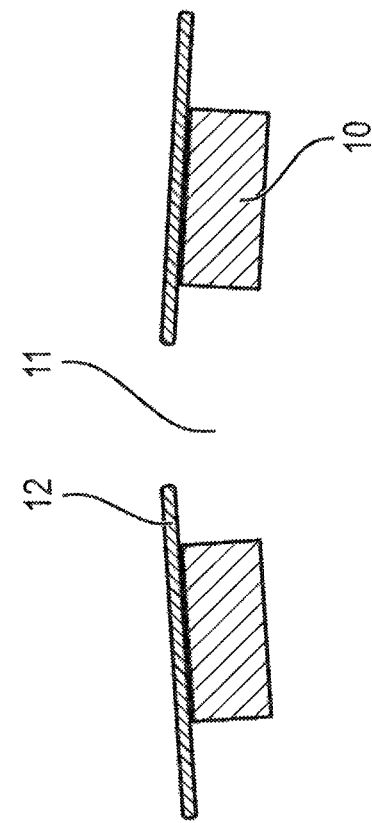
FIG. 2b is a cross-sectional view through two adjacent webs of a stent according to a preferred embodiment of the present invention in the implanted state.

Referring to the drawings in detail, wherein like numerals indicate like elements throughout the several views, FIG. 1b shows a partial cross-sectional view through a stent according to the present invention, wherein three adjacent lattice elements or webs 10 are illustrated, each of which having an associated contact element 12 as can also easily be identified in FIG. 2b. A web is understood in this case to be an elongated structural element of a stent which is joined to adjacent webs and enables the stent's deformation due to the movement relative to these webs. Contact element 12 has the function of transferring radial forces two-dimensionally from the stent to the adjacent vessel wall in the implanted state. To do this, contact element 12 has a continuous surface or is designed as a flat element. Specifically, contact element 12 comprises a foil, in particular a metal foil or a polymer foil. Other means for the two-dimensional transmission of radial forces are possible.

As illustrated in FIGS. 1b and 2b, contact element 12 is wider than associated web 10. Here the lateral edges of contact element 12 project beyond the web profile such that the contact area of individual web 10 and of the stent overall, which is effective for the transmission of force, is enlarged. In the embodiment according to FIGS. 1b and 2b, contact element 12 is arranged symmetrically or centrally to web 10. In this case, the lateral edges of contact element 12 protrude laterally over web 10 by the same amount (T-shape). Other configurations of contact element 12 in relation to web 10 are possible, for example, an L-shaped cross-section of contact element 12 and web 10 or intermediate shapes in which contact element 12 protrudes more over one side of the web than over the other side of the web.

The contact elements may be 10% to 500% wider than associated webs 10. The huge range arises because for different applications different oversizes of contact elements 12 lead to good results regarding enlargement of the contact area and good implantability of the stent. The person skilled in the art will determine the subranges appropriate in each case according to the requirements made on the stent. A range particularly suitable for the width of the contact elements is between 50 µm and 300 µm.

Contact elements 12 are designed to be flexible in respect of good implantability of the stent. The flexibility of contact elements 12 serves to make the contact area formed by contact elements 12 variable in such a manner that the contact area is smaller in the crimped state than in the expanded state. The variability of the contact area may be achieved by producing contact elements 12 from a shape memory material that is appropriately conditioned.

When designing the stent, both the flexibility and also the strength of contact elements 12 or of foils is important. Flexibility enables the stent to be deformed into the folded state. Wider contact elements 12 or foils may fill the space between webs 10 where there is a high level of flexibility, and thus good deformability. Furthermore, contact elements 12 or foils have sufficient strength to transmit the force to the vessel wall.

Figure 1A:
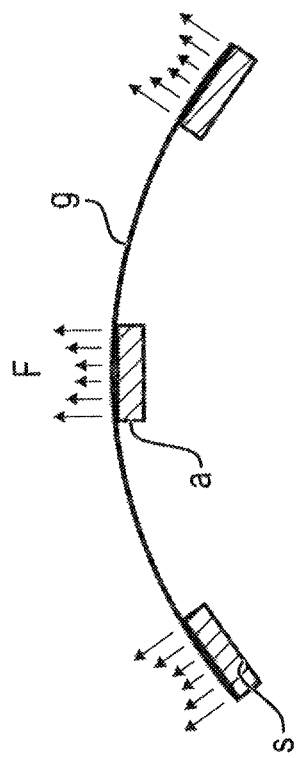
FIG. 1a is a partial cross-sectional view through a stent according to the prior art in an implanted state.

Furthermore, the flexibility of contact elements 12 or of foils has advantages with regard to the distribution of forces in the region of the webs by comparison with conventional stents in which higher pressures may occur on the margin of the stent than in the middle of the stent (FIG. 1a). This is due to the geometry of the webs which do not follow the blood vessel's rounded profile and therefore exert higher local pressures on very small contact points, e.g., on the edge of the webs. In contrast, due to their smaller wall thickness, significantly more flexible contact elements 12 or foils abut against the vessel wall such that there is virtually no formation of stress peaks and rather the pressure is exerted evenly on the vessel wall.

The height or wall thickness of contact element 12 (KE) is between 0.5 µm and 100 µm or generally between 0.5% and 50% of the height of each associated web 10 (GE). The person skilled in the art will select appropriate subranges depending on the size of the stent and/or the desired stability or flexibility of contact elements 12 and/or the weight of the stent. In the case of neurostents, i.e., stents for implantation in smaller, cerebral blood vessels, the height of webs 10 (GE) is generally between 50 µm and 90 µm. The height of contact elements 12 (KE) may accordingly be, for example, between 5 µm and 9 µm with a ratio of 1:10 (KE:GE).

The following characteristics should be considered overall when using foils for the creation of contact elements 12. The foil has a wall thickness that is small enough not to significantly increase the overall diameter of the system within the catheter. The foil's stiffness is adapted to exert a pressure on the vessel wall. The foil's flexibility enables the stent to be folded up inside the catheter. The joint between the foil and webs 12 (sic) is designed for the stress generally to be anticipated. The foil is biocompatible.

Given these characteristics, thin metal foils, for example made from NiTi-alloys, in particular Nitinol, are especially suitable for contact elements 12. Such metal foils have considerable strength even with very thin wall thicknesses.

Figure 2A:
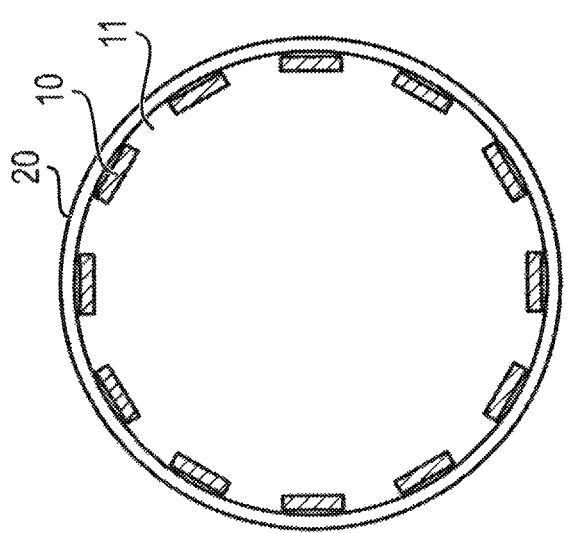
FIG. 2a is a cross-sectional view through a stent according to a preferred embodiment of the present invention in the implanted state.

FIG. 2a shows an overall cross-section through a stent in the implanted state whereby contact elements 12 are not illustrated for reasons of clarity. The stent has webs 10 distributed evenly around the circumference that abut against vessel wall 20 with each of their associated contact elements 12 (not illustrated) in such a manner that the stent adapts substantially to the blood vessel's contour. Webs 10 each delimit cells 11 that are shown as open spaces in the cross-sectional diagram. FIG. 2b shows a cross-section through two adjacent webs 10 each with an associated contact element 12. In the implanted state, cell 11 has a relatively large extension between webs 10 in the circumferential direction such that contact elements 12 are spaced apart from one another.

Figure 3B:
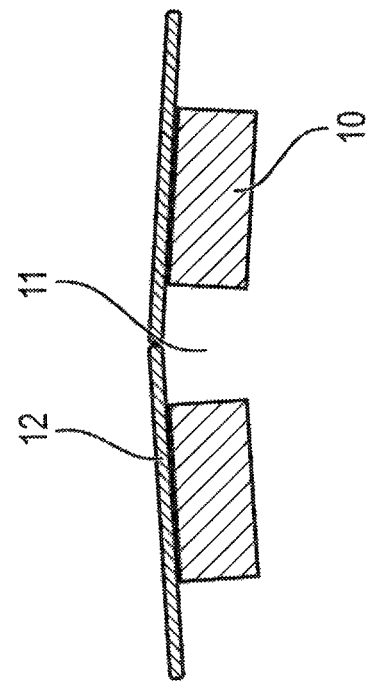
FIG. 3b is a cross-sectional view through two adjacent webs of a stent according to a preferred embodiment of the present invention in the compressed state.
Figure 3A:
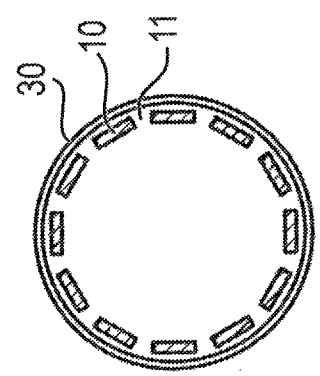
FIG. 3a is a cross-sectional view through a stent according to a preferred embodiment of the invention in a compressed state.

If the stent is present in the compressed state, cells 11 have a relatively small extension in the circumferential direction such that contact elements 12 touch one another (FIG. 3b). Webs 10 and contact elements 12 move closer together when the stent is compressed such that the result is a minimum cross-sectional diameter of the stent (FIG. 3a). In this manner it is possible to insert the stent into a catheter 30 that has a smaller cross-sectional diameter than the blood vessel into which the stent will be implanted. Again for reasons of clarity, no contact elements 12 are illustrated in FIG. 3a.

Figure 4A:
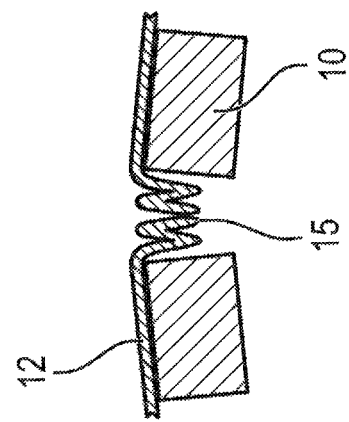
FIGS. 4a-e is in each case a cross-sectional view through two adjacent webs of a stent according to a preferred embodiment of the present invention in the compressed state.

FIGS. 4a-4e illustrate various embodiments of stents which are characterized by deformation of flexible contact elements 12 or of foils in the stent's compressed state:

According to FIG. 4a, contact elements 12 are disposed or adapted such that their regions protruding over the web profile overlap at least in part in the compressed state. In this case, one contact element 12 slides over an adjacent contact element 12 on crimping. Comparatively low flexibility of contact elements 12 is required for this since contact elements 12 or foils are only displaced by a small amount in the radial direction. In this case, the distance between webs 10 in the compressed state corresponds approximately to the oversize by which contact element 12 protrudes over the web profile. The web distance may be further reduced if there is additionally deformation of at least one of contact elements 12 or of foils.

Figure 4B:
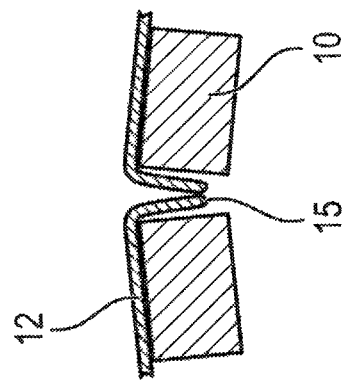

Contact elements 12 may be disposed or adapted in such a manner that they deform on compression and bend radially inwards (FIG. 4b). In this case, the protruding region of at least one of contact elements 12 protrudes into associated cell 11. In this case, contact elements 12 protrude beyond each associated web 10 or are bent over by no more than an amount that corresponds approximately to the height of web 10 to prevent the ends of bent over contact elements 12 from protruding into the flow cross-section.

Figure 4C:
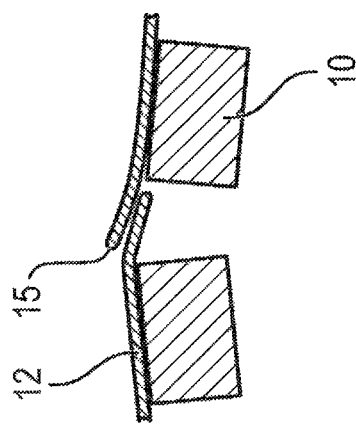

According to FIG. 4c, contact elements 12 between adjacent webs 10 are deformed in the tangential direction, in particular are folded, such that the region between webs 10 in the compressed state is filled by an arrangement of contact elements 12 that is substantially concertina-shaped in cross-section. In this case, the ends or longitudinal edges of contact elements 12 strike against the lateral surfaces of webs 10.

Figure 4D:
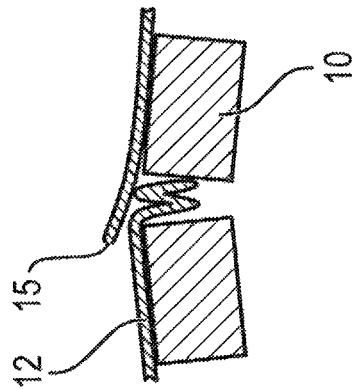
Figure 4E:
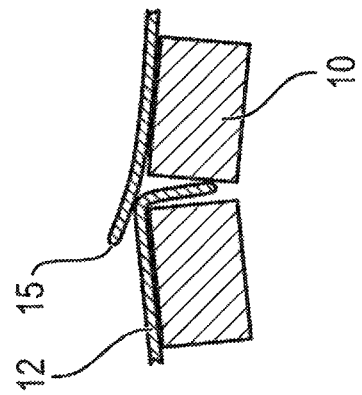

Combinations of the configurations of contact elements 12 referred to above are possible in the compressed state. For example, a contact element 12 may be bent radially inwards between two webs 10 and an adjacent or opposing contact element 12 may overlap contact element 12 bent inwards (FIG. 4d). According to FIG. 4e, a contact element 12 is deformed in the tangential direction between adjacent webs 10 whereby contact element 12 deformed in such a way is overlapped radially on the outside by a further contact element 12.

FIGS. 5a-d each show a view from above onto various cells 11 from each of which a stent is constructed or which are combined with each other in a stent. In this case, the cells of FIGS. 5a-d are each equal in size and delimited by webs 10. Contact elements 12 are disposed on webs 10 whereby the illustration is selected in such a manner that the direction of viewing is directed substantially outwards from underneath or from inside the stent such that both webs 10 and also contact elements 12 or foils disposed on the outer circumference and protruding laterally over webs 10 are visible. Cells 11 have a diamond shape, the longer diagonal of which extends in the stent's longitudinal direction and the shorter diagonal of which extends in the stent's circumferential direction.

In the embodiment according to FIG. 5a, contact elements 10 also delimit a diamond-shaped opening 13 which is adapted to or corresponds to the contour of cell 11. Individual contact elements 12 substantially comprise right-angled strips, in particular foil strips, that are disposed centrally on each web 10 or are disposed axisymmetrically to web 10 in its longitudinal direction. In this case, contact elements 12 protrude on both sides of webs 10 projecting beyond said webs by the same amount in each case such that the longitudinal edges of the contact elements are both parallel to one another and also parallel to web 10.

For example, contact elements 12 according to FIG. 5a are wider by approx. 300% than webs 10 such that they each protrude over the web profile on each side of the web by the width of web 10.

Contact elements 12 according to FIG. 5b are also wider than webs 10. Unlike the embodiment according to FIG. 5a, strip-like contact elements 12 are disposed obliquely, in particular diagonally, on webs 10. In this case, a first longitudinal edge 15 of contact element 12 terminates with a first longitudinal end of web 10. Second opposing longitudinal edge 15 of contact element 12 terminates with other second longitudinal edge 14 of web 10 (distance between web 10 and longitudinal edge 15 in each case=0). In the longitudinal direction of web 10, the distance between web 10 and first longitudinal edge 15 of contact element 12 increases while the distance between web 10 and second longitudinal edge 15 decreases in the same direction. This results in opening 13, which is delimited by contact elements 12, having a shorter diagonal 19 in the stent's longitudinal direction than each associated cell 11 and diagonal 18 is the same size in the circumferential direction as the diagonal of cell 11.

The sides of contact elements 12 projecting beyond webs 10 may therefore have a triangular shape, wherein both triangular-shaped sides separated by a web 10 may each be arranged offset, in particular symmetrically about a central point of web 10 (FIGS. 5b and 5c). In this case, the distance between a longitudinal edge 15 of contact element 12 and web 10 is zero at a longitudinal end 14 of web 10 while the distance between other longitudinal edge 15 and web 10 at same longitudinal end 14 is its maximum. Here, overall contact element 12 may have a substantially rectangular shape whereby contact element 12 is joined to web 10 along one of the diagonals of the rectangular shape.

It is also possible for both triangular-shaped sides to be disposed axisymmetrically to a longitudinal axis of web 10 such that the distance of both longitudinal edges 15 to each other at a longitudinal end 14 of web 10 corresponds to the width of web 10 and is greater on opposing longitudinal end 14 than the web width. Contact elements 12, in particular the sides of contact elements 12 projecting over the web width, may also have other shapes instead of the triangular shape. For example, the sides projecting over webs 10 may have a substantially rectangular design (FIGS. 5a and 5d).

FIG. 5c shows an embodiment in which contact elements 12 are also disposed obliquely or diagonally on webs 10, as already described in FIG. 5b, whereby, however, diamond-shaped opening 13 is formed in such a manner that longitudinal diagonal 19, i.e., the diamond shape's diagonal in the stent's longitudinal direction, is exactly as long as the longitudinal diagonal of cell 11 and circumferential diagonal 18, i.e., the diamond shape's diagonal in the stent's circumferential direction, is shorter than the circumferential diagonal of cell 11. Unlike the contact elements according to FIGS. 5a and 5b, the contact elements in the region of circumferential diagonals 18 of cell 11 are not joined together but have an interface 14 such that contact elements 12 can move apart from one another in this region when the stent is transferred into the compressed state. On compression of the stent, the longitudinal diagonal of cell 11 lengthens whereas the circumferential diagonal of cell 11 shortens. As a result, adjacent contact elements 12 are pulled apart in the region of the circumferential diagonals of cell 11. Interface 14 thus ensures at the same time that contact elements 12 are only slightly stretched or not stretched at all.

FIG. 5d shows an arrangement of contact elements 12 on lattice elements or webs 10, wherein opening 13 delimited by contact elements 12 is adapted in a diamond-shape to the contour of diamond-shaped cell 11. To this extent this embodiment corresponds to the illustration according to FIG. 5a. The difference from the embodiment according to FIG. 5a is that contact elements 12 according to FIG. 5d have a plurality of interfaces 14 that extend substantially perpendicularly from each of associated webs 10 along longitudinal edges 15 of contact elements 12. In this case, interfaces 14 of a cell 11 extend substantially in the same direction. As a result, contact elements 12 can slide over one another on compression of the stent such that contact elements 12 are arranged so as to overlap in the compressed state.

Generally, web widths of approx. 25-35 μm, in particular 30 μm, are provided for the stent according to the invention. The height of webs 10 may be between 50 and 90 μm, in particular 70 μm. In this case, the maximum spacing of webs 10 is preferably at most 500 μm, in particular ten times the web width. The ratio of the width of contact elements 12 to the width of lattice elements 10 is preferably at most 500%, i.e. that contact elements 12 project beyond web 10 on both sides of lattice elements 10 by an amount double the width of the lattice element or web 10. This embodiment relates to a stent for implantation in small vessels, in particular cerebral vessels whereby the invention is not restricted thereto. For use of the stent according to the invention in other, in particular larger, vessels, the person skilled in the art will generally choose other sizes and/or size ratios.

Using the stent described above, it is possible to ensure that the entire circumference of the stent in the implanted state can be enlarged beyond the extent disclosed previously in the prior art, whereby local radial forces F, which act on the vessel wall in the implanted state, are minimized. This is achieved in particular in that the effective contact area in the implanted state is increased which results in an even distribution of radial forces F.

Thus, with the stent according to the present invention, both a high number of webs and also a high web width is achieved. This results in an increase of the stent's overall circumference and thus a reduction of the local pressure acting on vessel wall 20. Overall, the circumference of the stent according to the present invention can be compressed or crimped in the implanted state, despite a relatively large circumference or a relatively large contact area, to a small circumference such that the stent can be implanted using a commercially available feeding system, in particular a catheter. This means that in the implanted state the stent's effective contact area is increased compared to previously known stents which have the same cross-sectional diameter in the compressed state.

A possible technique for the application or attachment of contact elements 12, in particular made of a nickel-titanium alloy, such as Nitinol, on lattice elements 10 is sputtering. In this case, the surface of the stent is bombarded with ions. It is possible to produce the special web cross-section (T or L shape) integrally, i.e. contact elements 12 and webs 10 in one piece, whereby production is preferably carried out by sputtering webs 10 and contact elements 12 in one piece. It is also possible to sputter contact elements 12 directly onto webs 10 of a previously produced lattice structure. In general, contact elements 12 may obtain their shape either during the sputtering process or may be formed in a further step, for example, by means of an etching process. In the second case, contact elements 12 or the foil are attached first of all around the entire circumference of the stent and subsequently openings 13 are made by etching. A suitable etching process is disclosed, for example, in German Patent Application No. DE 10 2006 029 831 A1 referring back to the applicant.

It is particularly advantageous if the method according to the present invention comprises the use of at least one sacrificial layer so that fast, series-compatible production of highly precise web geometries, in particular with high edge precision, is achieved. For example, German Patent Application No. DE 10 2006 007 231 A1, also referring back to the applicant, describes a method suitable for the integral production of a stent according to the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A stent having a tubular lattice structure, comprising:
a plurality of lattice elements (10) and cells (11) delimited by the lattice elements, wherein the lattice structure is transferred into a compressed state having a relatively smaller cross-sectional diameter and into an expanded state having a relatively larger cross-sectional diameter, and
a plurality of discrete flexible contact elements (12) adapted for transferring radial forces onto a vessel wall (20), wherein each discrete flexible contact element (12) is associated with a respective different lattice element (10), each flexible contact element (12) extending on an outer circumference of the respective associated lattice element (10) in a longitudinal direction of the lattice element (10), and each flexible contact element (12) being wider than the respective associated lattice element (10), at least in sections.

2. The stent according to claim 1, wherein the lattice elements in each case together with an associated contact element (12) form a substantially T-shaped or L-shaped cross-section, at least in sections.

3. The stent according to claim 1, wherein the contact elements (12) are in each case wider than each associated lattice element by at least 10%.

4. The stent according to claim 1, wherein the contact elements (12) are in each case wider than each associated lattice element by at most 500%.

5. The stent according to claim 1, wherein a width of one or a plurality of contact elements (12) is variable over a circumference and/or a length of the stent.

6. The stent according claim 1, wherein the cells (11) of the lattice structure each have an opening (13), which is delimited by the contact elements (12) of the lattice elements that form each cell (11).

7. The stent according to claim 6, wherein the openings (13) are adapted in each case to the contour of the cell (11).

8. The stent according to claim 6, wherein the openings (13) are substantially diamond-shaped.

9. The stent according to claim 8, wherein the contact elements (12) each have at least one longitudinal edge (15) which extends parallel to a longitudinal axis of each associated lattice element.

10. The stent according to claim 9, wherein the contact elements (12) each have at least one longitudinal edge (15) which is disposed at an angle to the longitudinal axis of each associated lattice element.

11. The stent according to claim 10, wherein the contact elements (12) each have two longitudinal edges (15) which are disposed parallel to one another and/or are disposed at an angle to a longitudinal axis of each associated lattice element.

12. The stent according to claim 11, wherein the contact elements (12) form substantially rectangular strips which are substantially disposed diagonally to each associated lattice element.

13. The stent according to claim 12, wherein the contact elements (12) are joined so as to be overlapping and/or adjacent to each other in corner regions of the cells (11) or are joined to each other.

14. The stent according to claim 13, wherein the contact elements (12) have a height between 0.5 µm and 100 µm.

15. The stent according to claim 14, wherein the height of the contact elements (12) corresponds to at least 0.5% of the height of each associated lattice element.

16. The stent according to claim 15, wherein the height of the contact elements (12) corresponds to at most 50% of the height of each associated lattice element.

17. The stent according to claim 16, wherein the height of one and/or a plurality of contact elements (12) is variable over a circumference and/or a length of the stent.

18. The stent according to claim 17, wherein the height of one and/or a plurality of contact elements (12) is variable over a width and/or a length of the contact elements (12).

19. The stent according to claim 18, wherein one and/or a plurality of contact elements (12) has a greater height in a region of each associated lattice element than in an outer region.

20. The stent according to claim 19, wherein the contact elements (12) comprise a shape memory material of a nickel-titanium alloy.

21. The stent according to claim 20, wherein the contact elements (12) have a structured surface of pores or grooves.

22. A method for the production of a stent according to claim 1, in which the flexible contact elements (12) are joined with the lattice elements or are produced integrally with the lattice elements in such a manner that at least one of the contact elements (12) is associated in each case with a lattice element, the contact element protruding beyond the lattice element's cross-section.

23. The method according to claim 22, wherein the contact elements (12) are joined to the lattice elements by means of laser beam micro welding.

24. The method according to claim 22, wherein the contact elements (12) are bonded to the lattice elements.

25. The method according to claim 22, wherein the contact elements (12) are produced by means of magnetron sputtering or ion beam sputtering.

* * * * *